(12) United States Patent
Doci

(10) Patent No.: US 9,782,293 B2
(45) Date of Patent: Oct. 10, 2017

(54) IMPLANT FOR TREATING GLAUCOMA

(71) Applicant: Doci Innovations GmbH, Sieksdorf (DE)

(72) Inventor: Violeta Doci, Hamburg (DE)

(73) Assignee: Doci Innovations GmbH, Sierksdorf (DE)

( * ) Notice: Subject to any disclaimer, the term of this patent is extended or adjusted under 35 U.S.C. 154(b) by 0 days.

(21) Appl. No.: 14/430,320

(22) PCT Filed: Sep. 30, 2013

(86) PCT No.: PCT/EP2013/070367
§ 371 (c)(1),
(2) Date: Mar. 23, 2015

(87) PCT Pub. No.: WO2014/049174
PCT Pub. Date: Apr. 3, 2014

(65) Prior Publication Data
US 2015/0216729 A1    Aug. 6, 2015

(30) Foreign Application Priority Data
Sep. 28, 2012    (WO) .................. PCT/IP2012/001937

(51) Int. Cl.
*A61M 37/00*    (2006.01)
*A61F 9/007*    (2006.01)
(52) U.S. Cl.
CPC ................................ *A61F 9/00781* (2013.01)
(58) Field of Classification Search
CPC .................................................. A61F 9/00781

USPC ........................................................ 604/8, 9
See application file for complete search history.

(56) References Cited

U.S. PATENT DOCUMENTS

| 7,678,065 B2 | 3/2010 | Haffner et al. |
| 7,740,604 B2 | 6/2010 | Schieber et al. |
| 7,951,155 B2 | 5/2011 | Smedley et al. |
| 2004/0193262 A1* | 9/2004 | Shadduck ........... A61F 9/00781 623/4.1 |

(Continued)

OTHER PUBLICATIONS

International Search Report for PCT/EP2013/070367 mailed Nov. 28, 2013.

*Primary Examiner* — Philip R Wiest
(74) *Attorney, Agent, or Firm* — Drinker Biddle & Reath LLP

(57) ABSTRACT

The invention relates to an implant for reducing ocular hypertension. Said implant can be used in particular to prevent and treat glaucomas that are emerging or occur. In particular, the implant is an implant (10) for the Schlemm's canal, which comprises a bridge (20), which has a first end point (22) and a second end point (24) and a first support region (26), a second support region (28), and a connecting piece (30), the bridge (20) extending along a first line (L1) from the first end point (22) to the second end point (24) across the first support region (26), the connecting piece (30), and the second support region (28) and the connecting piece (30) having a first cross-sectional area on average along the first line (L1) and the first support region (26) having a second cross-sectional area on average along the first line (L1) after the implantation, characterized in that the second cross-sectional area is at least 50% larger than the first cross-sectional area.

19 Claims, 7 Drawing Sheets

(56) References Cited

U.S. PATENT DOCUMENTS

2008/0183121 A2* 7/2008 Smedley ............. A61F 9/00781
 604/8
2011/0224597 A1 9/2011 Stegmann et al.
2014/0066833 A1* 3/2014 Yaron ................. A61F 9/00781
 604/9

* cited by examiner

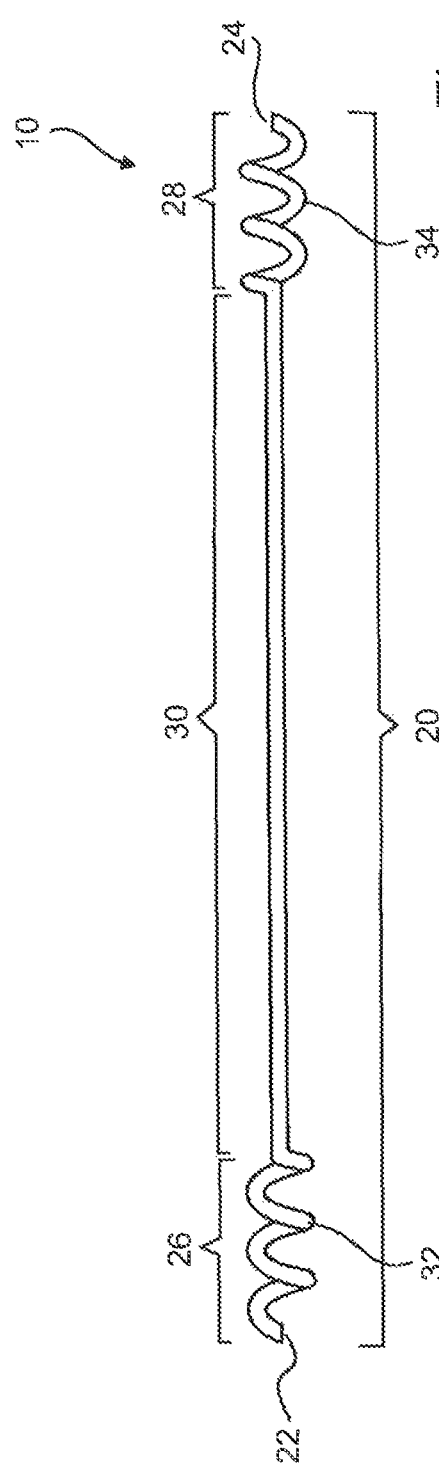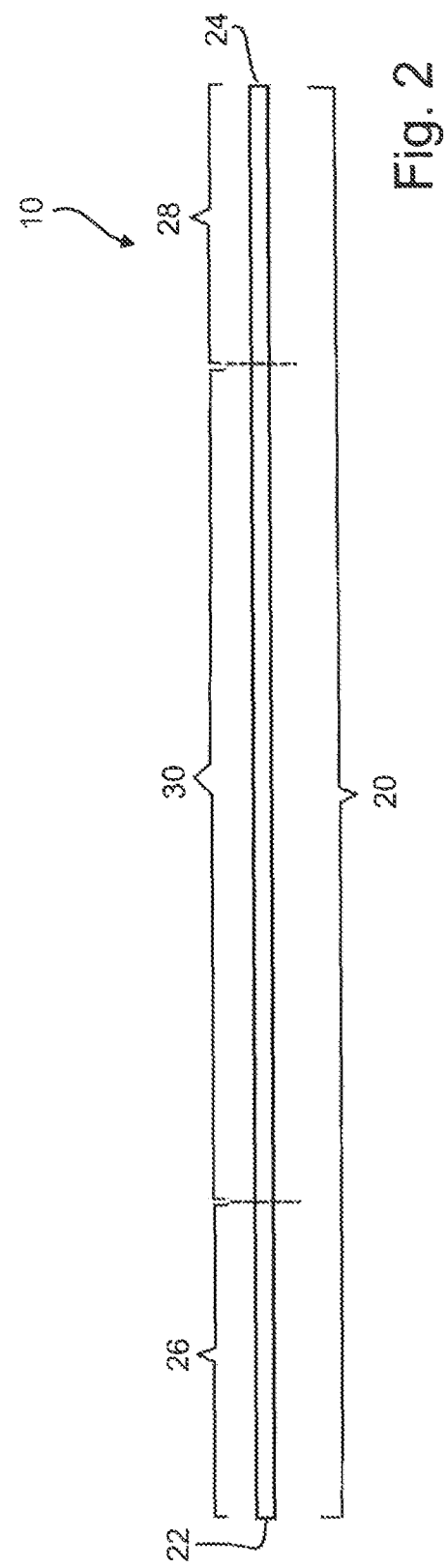

IMPLANT FOR TREATING GLAUCOMA

CROSS-REFERENCE TO RELATED APPLICATIONS

This application is a national stage application (under 35 U.S.C. §371) of PCT/EP2013/070367, filed Sep. 30, 2013, which claims benefit of International Application No. PCT/IB2012/001937, filed Sep. 28, 2012, both of which are incorporated herein by reference in their entirety.

FIELD OF THE INVENTION

The present invention relates to an implant for reducing intraocular tension. This implant can be used in particular to prevent and treat glaucomas that are emerging or occur.

BACKGROUND OF THE INVENTION

Glaucomas (also referred to as green star) are a widespread eye disease. The damage to the optic nerve associated with this disease is produced by hypertension in the eye. This hypertension can be reduced surgically. There are a large number of approaches for the treatment of glaucomas. One possible treatment is the implantation of appropriate implants, which are also referred to as stents.

US patent application US 2007/0118147 discloses an implant that is to be inserted into the Schlemm's canal. This implant has a type of tube system. A first tube has an inlet opening. This tube is connected via a connection piece to a transverse tube. This transverse tube has a number of outlets. The purpose thereof is to dispense fluid.

A disadvantage of this implant however is that it is rather bulky on the whole and is also space-consuming, that is to say has a considerable extension in a number of spatial directions. In this regard the insertion of the implant is not entirely without risk for the surgeon, and in addition correct orientation appears to be very important, and a long healing period is to be expected after insertion.

US patent application US 2005/0119636 discloses another implant, which is also to be inserted into the Schlemm's canal. This implant essentially has the form of an elongate tube. There is thus an inlet and an outlet opposite the inlet.

US patent application US 2004/0193262 A1 describes a stent that can be fabricated from a shape-memory alloy. This stent has the classic function of widening vessels following insertion of said stent. It can adopt various forms for this purpose, for example a branch-like form or also a spiral form. It is disclosed in the patent application that the stent is to be inserted into the trabecular meshwork and is to expand same. The stent is dimensioned in such a way that it can protrude completely through the Schlemm's canal. There is supposedly also an improved discharge through the Schlemm's canal. However, due to its size alone, the stent is not suitable for stabilising the Schlemm's canal. Rather, the Schlemm's canal is pressed, or the shape thereof is modified undesirably. Such potential disadvantages in the event of liquid transport are counteracted with the stent from this US patent application in that the stent itself is a hollow body, and liquid can thus be drained through the stent.

The present invention seeks to improve the prior art. It offers an implant for insertion into the Schlemm's canal, said implant having small dimensions and thus being easily and reliably insertable and ensuring a reliably predictable and controllable drainage of eye fluid.

In the present case this is thus an implant for the Schlemm's canal, i.e. an implant that is suitable at least for partial implantation into the Schlemm's canal and that is optimised for the partial implantation into the Schlemm's canal. The dimensions of the implant are thus selected such that said implant can be inserted at least in part or even also completely into the Schlemm's canal. The corresponding cross section of the implant should therefore preferably be smaller than the cross section of the Schlemm's canal perpendicularly to the peripheral direction thereof, or in any case should be small enough for the implant to be inserted through this cross section of the Schlemm's canal.

The implant should have a bridge, which in turn has a first end point, a second end point, a first support region, a second support region and a connecting piece. Here, the bridge should extend along a first line from the first end point to the second end point across the first support region, the connecting piece and the second support region. Here, the first support region advantageously borders the first end point and the second support region borders the second end point. At least the connecting piece can be flexible. The first line therefore does not have to be a line running in straight line. The line, however, describes the primary direction of extension or primary axis of the respective component parts. A cross-sectional area that presents a minimal cross section of the component parts compared to the cross-sectional areas titled relative to the line is thus produced perpendicularly to this line in each case.

Along this first line the connecting piece has a first cross-sectional area on average. The average cross-sectional area can be calculated for example from a plurality of cross-sectional areas by forming the arithmetic mean. The first cross-sectional area describes a measured value that for example can be specified in square millimeters, which corresponds to this arithmetic mean.

Similarly, an average cross-sectional area can be assigned to the first support region and is referred to herein as the second cross-sectional area. When determining the second cross-sectional area, the form of the first support region following the implantation is used as a basis. As will be explained hereinafter in greater detail, the first support region can be transferred into another (substantially more slender) form for the purpose of easier implantation, and the cross-sectional region then adopts its ultimate form only following implantation.

In the context of the invention the second cross-sectional area should be at least 50% larger than the first cross-sectional area. It may be expedient if the second cross-sectional area is larger by more than 75%, 100%, 150%, 200%, 300%, 400%, 500% or more, wherein the difference may generally remain below 2000%.

It is generally expedient to provide an implant with which the second support region also has a much larger cross-sectional area than the first cross-sectional area. The second support region, following implantation, has a third cross-sectional area along the first line on average. This third cross-sectional area should be at least 50% larger than the first cross-sectional area. In addition, the size difference percentages specified above with respect to the second cross-sectional area and the first cross-sectional area are also advantageous.

The second and third cross-sectional areas should be approximately 10,000 µm$^2$ to 100,000 µm$^2$ in size. This generally allows good insertion into the Schlemm's canal.

Based on the form that the first support region, but also the second support region can adopt for implantation, it is advantageous if the corresponding cross-sectional areas are not very much larger than the first cross-sectional area. It is expedient if the first support region for implantation can be transferred into a position in which it has along the first line a fourth cross-sectional area on average, which is no more than 40% larger than the first cross-sectional area. Accordingly, it is also useful if the second support region for implantation can be transferred into a position in which it has along the first line a fifth cross-sectional area on average, which is no more than 40% larger than the first cross-sectional area. It may be expedient if the fourth and the fifth cross-sectional area of the first cross-sectional area are substantially identical to the first cross-sectional area.

The transition from a form of the support region favourable for the implantation to a form of the support region favourable after implantation can be made in that the first and/or the second support region after implantation adopt a spiral form. Prior to the implantation, the first and/or the second support region may adopt a stretched form. Here, they may adopt a stretched cylinder form, for example, and in their form may continue the cylinder form of the connecting piece.

In order to produce this transition, it is useful if the first and/or the second support region is/are fabricated from a shape-memory material or a shape-memory alloy. Such materials are sometimes also referred to as memory materials or memory alloys. The materials can be transferred from a first form into a second, also rather more complex form without the second form resembling the first form in any way. This can be achieved for example by temperature change. In the case of a typical shape-memory alloy it is possible for this to adopt a stretched form in the cooled state, and with heating to adopt a predefined form, for example a spiral form. A thermal effect acting in this direction is particularly favourable for an operation on humans. The implant can be suitably cooled prior to the insertion and will quickly adopt its second form in the body as a result of body heat.

As is yet to be explained in greater detail, the connecting piece of the implant should substantially follow the curved form of the Schlemm's canal. To this end it is advantageous if the connecting piece is flexible. It is also advantageous if the connecting piece has a lower flexural rigidity compared to the first and/or the second support region. (In other words the bending of a portion of the connecting piece in response to a certain test force should be greater than the bending of a portion of a support region of identical length exposed to the same test force). This should be the case in particular in the form of the implant after implantation. Following implantation, the support regions should ensure a fixed anchoring in portions of the Schlemm's canal, whereas the connecting piece should adopt a curved form without great resistance.

It is also advantageous if the connecting piece is not extendible or compressible along the axis of extension thereof. In this way, the connecting piece with fixed extension ensures that the distance between the first and second support region remains constant. A connecting piece that is neither extensible nor compressible is also referred to herein as being distance-stable.

A connecting piece that is relatively long on the whole is favourable. The length of the connecting piece may thus surpass the diameter thereof by the factor 10, but possibly also by a factor of 20 or 30. A factor of more than 50, however, is not necessary. The connecting piece may advantageously have a maximum diameter from 5 to 150 m. The connecting piece expediently may be fabricated from a round wire with a diameter from 5 to 150 m or 10 to 150 m.

In the case of the concept of the implant according to the present invention the bridge must not conduct fluid. It is therefore expedient to form the bridge (but at least the connecting piece) without cavities, that is to say solid.

Besides the bridge, the implant may also comprise other elements. Here, fluid conduction devices can be considered in particular. Such fluid conduction devices can be provided in the form of tubes. Besides the bridge, an implant according to the invention may thus also comprise at least one tube.

An implant is expedient which, after implantation, can adopt a position in which the first line is curved and thus runs in a first plane, wherein the implant has at least one tube, which enables fluid conduction through this first plane.

In the context of the invention it is generally advantageous to equip a bridge with fluid conduction devices, which enable a partial fluid conduction perpendicular to the plane of the bridge. These tubes can be cylindrical tube proportions in the conventional manner. However, it is also possible to provide a tube as a spiral wire coil. If, for example, the connecting piece is formed as a thin wire, this wire can be wound spirally in order to produce a fluid conduction device of the described type. Alternatively, the tubes for example can be integrated in the connecting piece by interrupting said connecting piece into a plurality of portions and interconnecting individual portions of adjacent tubes. To this end, inter alia, a connection by adhesive bonding or soldering is conceivable. The one-piece embodiment of fluid conduction devices and bridge is also advantageous.

In order to enable a fluid conduction through the first plane, the at least one can be oriented exactly or at least substantially perpendicularly to the first plane. The desired effect, however, is also achieved with deviations from the perpendicular, in particular if the angle to the perpendicular this is less than 45°, or less than 30°, or less than 10°.

The tubes may have a diameter that is small compared to the connecting piece. By way of example, it is sufficient if the diameter of the least one tube is less than 10% or also 5% of the length of the first connecting piece. In this way a plurality of tubes can be accommodated over the length of the first connecting piece, for example two, three, four or five tubes. Such tubes can be fabricated from metal or also plastic. The materials can be similar or identical to those used for the bridge.

In the context of the present invention an implant can thus be provided that is suitable for surgical glaucoma treatment, which can be inserted into the frontally opened Schlemm's canal, and which has arcuate protrusions or tubes, which can be pressed into openings of the collecting ducts for aqueous humour. Such an implant may comprise spiralled support regions made of a shape-memory material.

The advantages of the implant according to the invention as well as the differences compared to known implants will become clear most easily in conjunction with the drawings, in particular also drawings of the anatomy of the eye. These aspects therefore will be discussed in greater detail hereinafter in conjunction with the drawings.

These features of the invention are described in combination in the figures and in the associated descriptions. However, these features can also be comprised in other combinations by an object according to the invention. Each disclosed feature is thus also to be considered as disclosed in technically feasible combinations with other features. The figures are slightly simplified and schematic in part.

FIG. 1 shows an implant according to the invention in a storage configuration;

FIG. 2 shows a corresponding implant in a configuration immediately prior to implantation;

Figure 3:
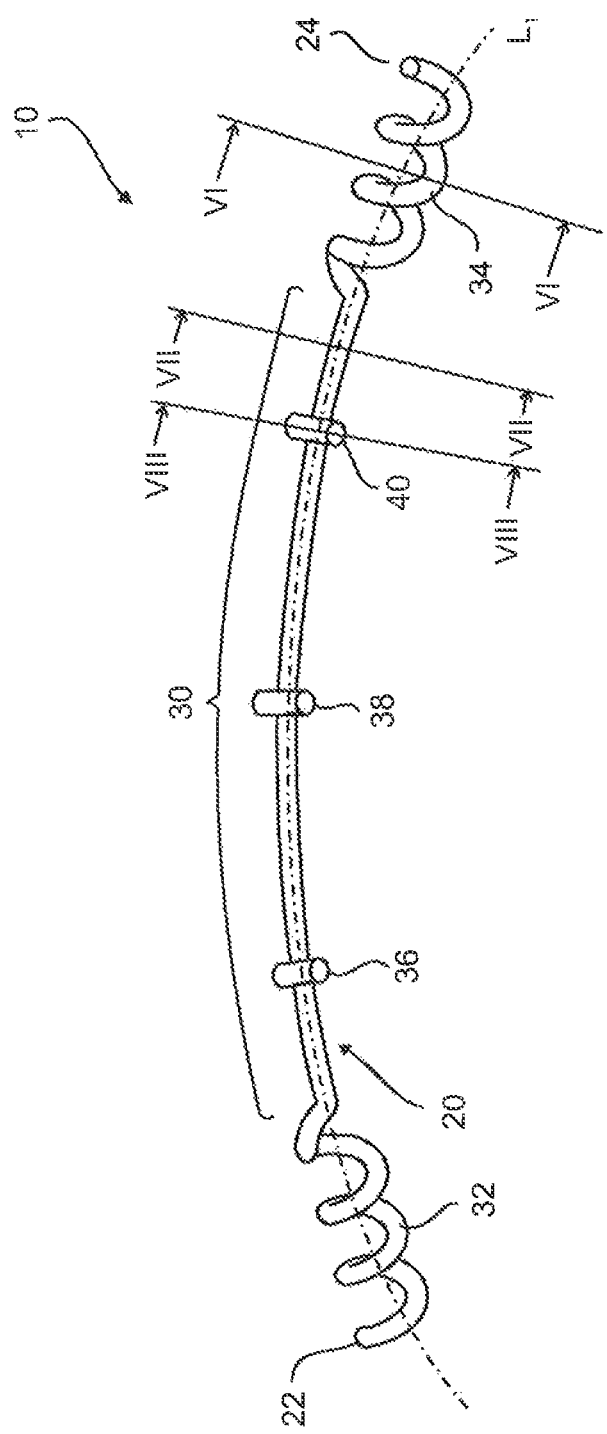
FIG. 3 shows another implant according to the invention in a configuration that corresponds largely to the position adopted following implantation.

FIG. 1 shows an implant according to the invention in a configuration in which it could be stored, for example. The implant in this embodiment consists only of the bridge 20. The bridge 20 has a first end point 22 to the left. This is adjoined by a first support region 26. The second end point 24 is located opposite, in a mirror image, and is adjoined by the second support region 28. Both support regions are interconnected by a connecting piece. The support regions are spiralled in this configuration, such that a first spiral 32 is located in the first support region and a second spiral 34 is located opposite in the second support region 28.

FIG. 2 shows the same implant in another configuration. The implant can be brought into this configuration immediately prior to an operation. The implant has no spiralled ends, but the first support region 26 and the second support region 28 each have the form of stretched round pieces. They join the connecting piece 30 integrally and in a form-fitting manner. The implant can be transferred into such a form by cooling, for example.

FIG. 3 shows another implant according to the invention. This has the component parts of the bridge that are already known. This implant, however, additionally has three tubes, which are arranged equidistantly on the connecting piece 30. As a result, the distance between the first tube 36 and the second tube 38 is exactly the same as the distance between the second tube 38 and the third tube 40. An equidistant arrangement of the tubes is advantageous, but is not absolutely necessary. These tubes are used as a fluid conduction device, and the more precise function thereof will be illustrated in greater detail hereinafter based on the anatomy of the eye. The broken lines transverse to the line of extension of the bridge 20 are reproduced based on the implant 10 and will be illustrated hereinafter in FIG. 6 and FIG. 7 and FIG. 8.

In FIG. 3 the bridge is shown on the whole in a curved position. Here, the connecting piece 30 is curved in particular. In this curved position, the implant adapts particularly well to the course of the Schlemm's canal.

As shown in FIGS. 1-3 the first end point (22) and the second end point (24) are the longitudinally outermost portions of the implant. FIG. 3 also illustrates the support regions (26,28) to have a spiral form which is formed radially around the first line (L1).

Figure 4:
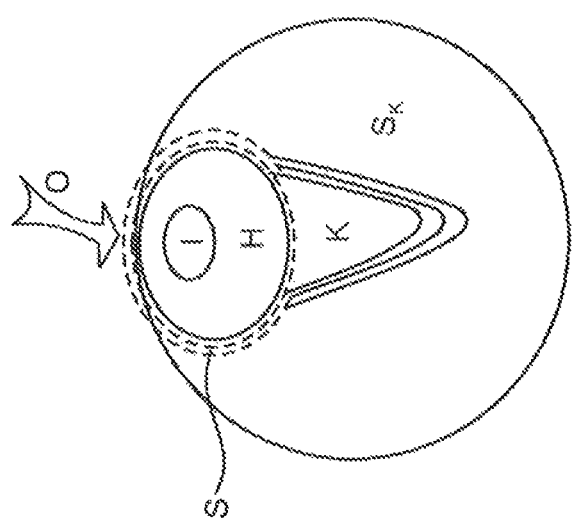
FIG. 4 shows a schematic perspective illustration of a human eye.

FIG. 4 shows a schematic perspective illustration of the eye. At the top, the cornea H can be seen, and in the middle thereof the iris I. The cornea is surrounded by the sclera Sk.

In order to enable an improved discharge of the aqueous humour, surgical access to the Schlemm's canal S may have to be found. An appropriate operation would conventionally be carried out from outside. Here, a significant part of the sclera Sk would be opened. This could occur in a conventional operative field K. As indicated in the drawing, the operative field could be selected to be larger or smaller depending on the angle over which the Schlemm's canal should be made accessible.

The implant of the present invention, however, should be used in conjunction with a minimally invasive operation. This is a key aspect in order to acknowledge the advantages of the present invention. The implant has very small dimensions and is suitable for implantation involving minimal surgery. The general operation direction here is the direction O. The access to the Schlemm's canal S is thus found perpendicularly through the cornea.

Figure 5:
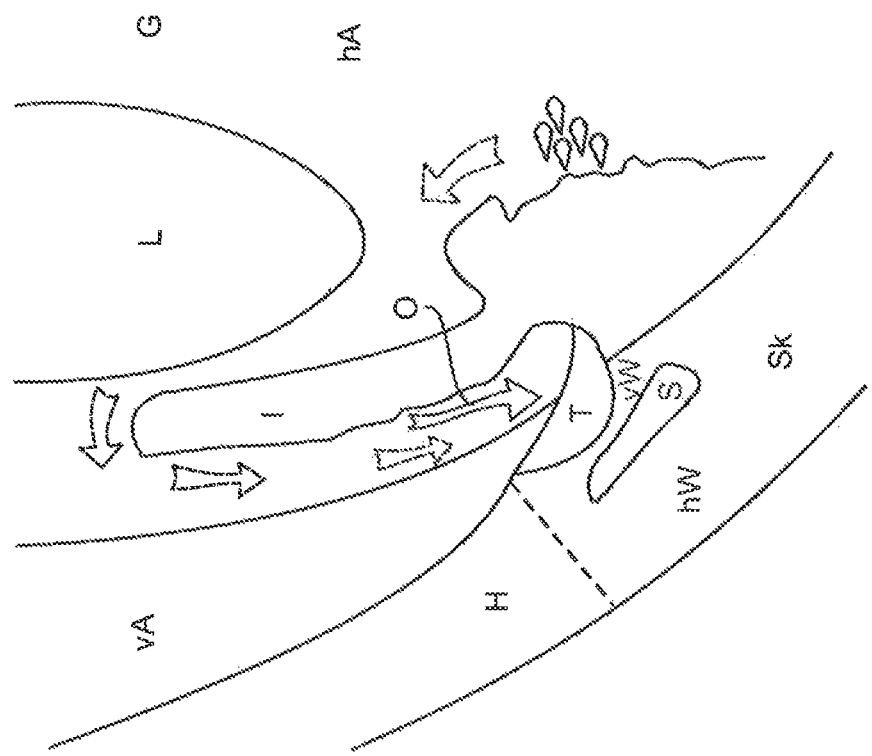
FIG. 5 shows a cross-sectional illustration of a region of the human eye.

The parts of the eye important for comprehension of the present invention are also reproduced in the overall illustration of FIG. 5. This is a cross-sectional illustration in which the posterior chamber of eyeball hA and the vitreous humour G of the eye are located on the right-hand side and the cornea H is located on the left-hand side. The lens L and the iris I are located therebetween.

Aqueous humour finds its way from the direction of the vitreous humour past the lens L and flows around the iris I, such that the aqueous humour passes from the posterior chamber of eyeball hA into the anterior chamber of eyeball vA. In the case of a healthy eye it is then forwarded on through the trabecular meshwork. The trabecular meshwork T transitions into the front wall vW of the Schlemm's canal S (wherein this transition is without sharp boundary). The Schlemm's canal lies in the sclera Sk. It is delimited outwardly by a rear wall hW (from the viewpoint of the surgeon).

Figure 6:
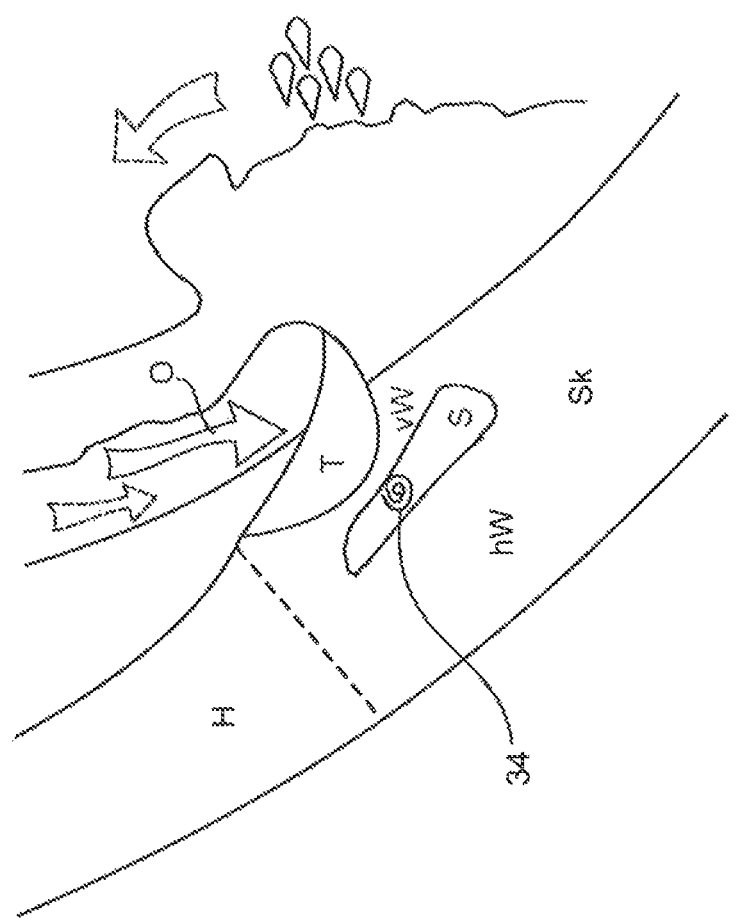
FIG. 6 shows a corresponding, but enlarged cross-sectional illustration of a cross-section through the eye following insertion of the implant.

FIG. 6 shows an enlarged detail from FIG. 5. In this detail a surgical technique is sketched, which plays a role in conjunction with the present invention. In the case of a glaucoma patient the trabecular meshwork T is no longer permeable to aqueous humour or is no longer sufficiently permeable to aqueous humour. This therefore can no longer be drained through the Schlemm's canal. It is possible in a minimally invasive intervention to remove part of the trabecular meshwork (substantially by scalpel and also heat action). A very advantageous surgical instrument for such an intervention is the trabectome. This occurs from the direction of surgery O. Here, parts of the front wall vW of the Schlemm's canal S can also be removed. The removal occurs here over a limited angular range, for example over 30°, 45° or also 90° and is also indicated in FIG. 4. (The angles are thus based on the angle of 360° covered by the Schlemm's canal as circular vessel.)

This surgical technique leaves behind minimal damage on the eye and has proven to be very effective. However, the long-term effect of the operation is not always completely satisfactory.

In conjunction with the present invention it has been identified that the remaining Schlemm's canal cannot always perform its function efficiently. As has been identified, a deficient mechanical stability of the remaining Schlemm's canal contributes to this.

The implant of the present invention can be used at the point at which the Schlemm's canal was removed. The implant length is thus to be matched to the length of the Schlemm's canal. In an adult the Schlemm's canal typically has a diameter from 12 to 14 mm. Accordingly, the Schlemm's canal typically has a circumference from 50 to 75 mm. If, in the case of a Schlemm's canal of 50 mm circumference, an angular segment of 30° is removed, a gap of a good 4 mm would thus remain. The implant should then have a length of more than 4 mm. It is generally expedient if, for described case, the connecting piece has a length of exactly 4 mm and the support regions each have a length of approximately 1 mm. These specified length are only approximate, and a surgeon will choose an implant for the respective application under consideration of many auxiliary conditions.

Since the first support region is inserted in a first opened portion of the Schlemm's canal and the second support region is inserted in a second opened remaining region of the Schlemm's canal, a strong mechanical stabilisation is achieved.

A distance-stable connecting piece contributes to this and fixes the position of the resultant end piece of the Schlemm's canal on the circumferential line around the cornea.

The mechanical stabilisation of the remaining end portions of the Schlemm's canal in the direction of the cross section shown in FIG. 5 is just as important.

This effect can be seen once more in FIG. 6. The support region is inserted into the Schlemm's canal S such that this better withstands pressure which is effective within the plane of illustration.

Figure 7:
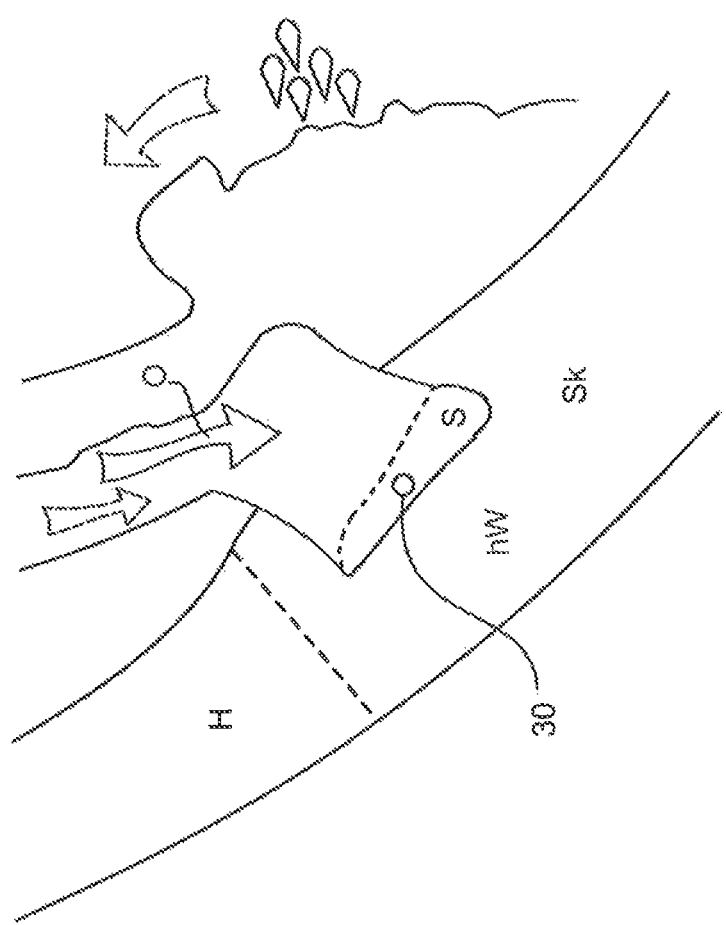
FIG. 7 shows, in a view corresponding to FIG. 6, a displaced parallel cross section through the eye.

FIG. 7, with a further cross-sectional view, shows the position of the implant. As indicated in FIG. 3, only a cross-sectional area through the connecting piece 30 can be seen in this view.

Figure 8:
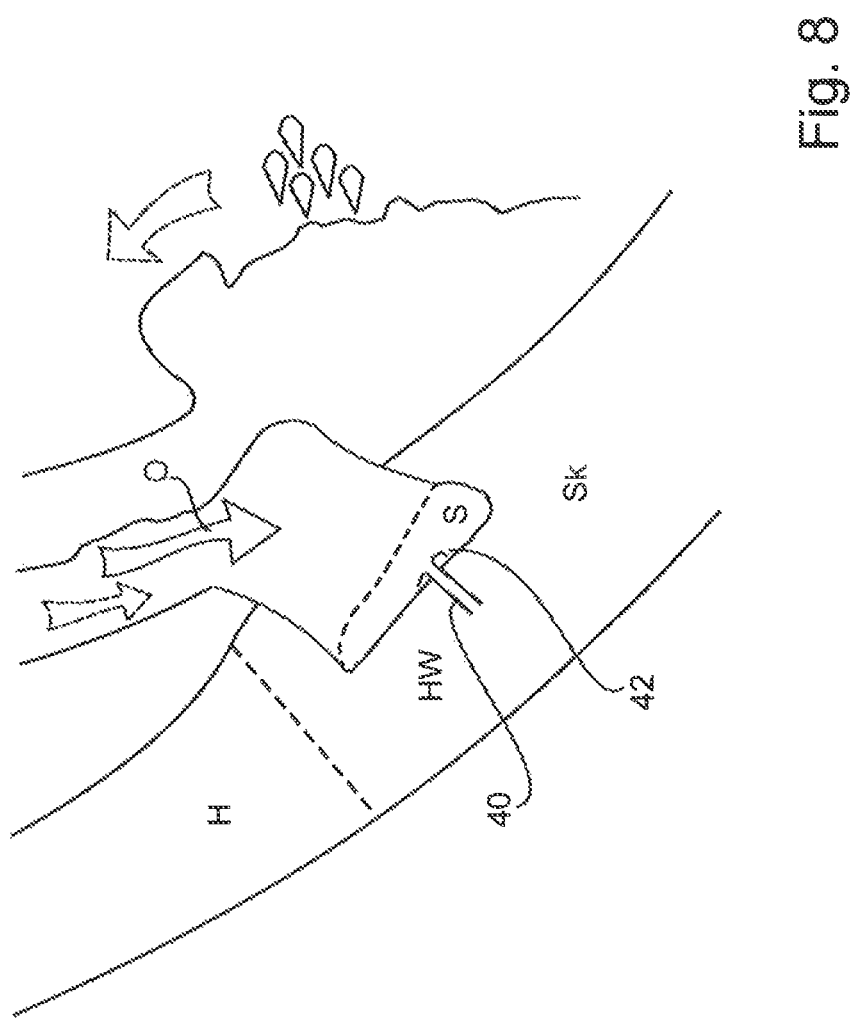
FIG. 8 shows, in a cross-sectional view displaced compared to FIG. 6 and FIG. 7, a further cross section through the eye.

FIG. 8 shows a further cross-sectional view. In this cross-sectional view the position of a tube 40 can be seen. This tube is introduced into the tissue of the rear wall hW. It is advantageously fitted precisely in a collecting duct located there. The tube diameter for the purpose should be 20% to 50% larger than the diameter of the collecting duct.

It is advantageous if the tube protrudes over approximately 20% to 30% of the length thereof from the tissue (i.e. into the region of the opened Schlemm's canal). This prevents tissue from growing into the tube and closing said tube. The tube 40 can also be equipped with an edge 42, which also helps to hold tissue away from the tube inlet.

It has also proven to be advantageous if the tubes have smooth walls, since otherwise an unfavourable intergrowth with tissue or also an ingrowth of the newly created fluid drainage path would be observed.

The description has also made it clear that the implant according to the invention is not a stent in the conventional sense. A stent in the conventional sense is used to widen a vessel, for example a blood vessel, so as to thus improve the flow of fluid therethrough. The present implant by contrast bridges a gap created by removal of vessel material. In this respect the function of said implant goes beyond that of a stent.

Within the scope of the invention it has been found that when bridging such a gap in the Schlemm's canal a key additional effect is provided. In the regions in which parts of the Schlemm's canal have been removed and damage to the tissue by mechanical influence or by heat potentially also cannot be ruled out entirely, an improved fluid drainage is achieved. Fluid is conducted into the rear wall and therefore into the sclera Sk. From there, the fluid is drained regularly. This is achieved already by an implant without tubes, but particularly by an implant with tubes.

On the whole it has been made clear how the effects of a minimally invasive operation could be considerably improved with the implant according to the invention. These improvements concern the volume of the aqueous humour drainage, but also the stability over time of the effect.

LIST OF REFERENCE SIGNS 10 implant
20 bridge
22 first end point
24 second end point
26 first support region
28 second support region
30 connecting piece
32 first spiral
34 second spiral
36 first tube
38 second tube
40 third tube
42 edge
hA posterior chamber of eyeball
vA anterior chamber of eyeball
G vitreous humour
H cornea
I iris
K conventional operative field
L lens
O minimally invasive direction of operation
T trabecular meshwork
Sk sclera
S Schlemm's canal
vW front wall of the Schlemm's canal
hW rear wall of the Schlemm's canal
L1 first line
E1 first plane

The invention claimed is:

1. An implant (10) for implantation into the Schlemm's canal, said implant comprising a bridge (20) with a first end point (22) and a second end point (24) and a first support region (26), a second support region (28) and a connecting piece (30), wherein the bridge (20) extends along a first line (L1) from the first end point (22) to the second end point (24) across the first support region (26), the connecting piece (30) and the second support region (28), wherein the first end point (22) and the second end point (24) are the longitudinally outermost portions of said implant, and wherein the connecting piece (30) has a first cross-sectional area on average along the first line (L1) and the first support region (26) following implantation has a second cross-sectional area on average along the first line (L1), characterised in that the second cross-sectional area is at least 50% larger than the first cross-sectional area, and at least the connecting piece (30) is solid without cavities.

2. The implant (10) according to claim 1, wherein the second support region (28) following implantation has a third cross-sectional area on average along the first line (L1), and the third cross-sectional area is at least 50% larger than the first cross-sectional area.

3. The implant (10) according to claim 1, wherein the first support region (26) for implantation can be transferred into a position in which said implant along the first line (L1) has a fourth cross-sectional area on average, which is no more than 40% larger than the first cross-sectional area.

4. The implant (10) according to claim 1, wherein the second support region (28) for implantation can be transferred into a position in which it has along the first line (L1) a fifth cross-sectional area on average, which is no more than 40% larger than the first cross-sectional area.

5. The implant (10) according to claim 1, wherein the first support region (26) and/or the second support region (28) adopt/adopts a spiral form following implantation.

6. The implant (10) according to claim 1, wherein the first support region (26) and/or the second support region (28) is/are fabricated from a shape-memory alloy.

7. The implant (10) according to claim 1, wherein the connecting piece (30) is flexible.

8. The implant (10) according to claim 1, wherein the connecting piece (30) has a lower flexural rigidity compared to the first support region (26).

9. The implant (10) according to claim 1, wherein the connecting piece (30) is distance-stable.

10. The implant (10) according to claim 1, wherein the length of the connecting piece (30) exceeds the diameter thereof by a factor of at least 10.

11. The implant (10) according to claim 1, said implant after implantation adopting a position in which the first line (L1) is curved and runs in a first plane (E1) and has at least one tube (36), which enables fluid conduction through the first plane (E1).

12. The implant (10) according to claim 11, wherein the at least one tube (36) has a diameter which makes up less than 10% of the length of the connecting piece (30).

13. The implant (10) to prevent and treat an increased intraocular tension and/or glaucoma according to claim 1.

14. Use of an implant (10) according to claim 1 to prevent and treat an increased intraocular tension and/or glaucoma.

15. The implant according to claim 11 wherein said at least one tube (36) is oriented perpendicularly to the first plane (E1).

16. The implant (10) according to claim 2, wherein the first support region (26) for implantation can be transferred into a position in which said implant along the first line (L1) has a fourth cross-sectional area on average between the first and the second cross-sectional areas, which is no more than 40% larger than the first cross-sectional area, and wherein the second support region (28) for implantation can be transferred into a position in which it has along the first line (L1) a fifth cross-sectional area on average between the first and the third cross-sectional areas, which is no more than 40% larger than the first cross-sectional area.

17. The implant (10) according to claim 2, wherein the second and the third cross-sectional areas are from 10,000 µm² to 100,000 µm².

18. The implant (10) according to claim 1, wherein the second cross-sectional area is at least 75% larger than the first cross-sectional area.

19. The implant (10) according to claim 5, wherein the spiral form is a spiral formed radially around the first line (L1).

* * * * *